United States Patent [19]

Müller et al.

[11] Patent Number: 5,663,447
[45] Date of Patent: Sep. 2, 1997

[54] PROCESS FOR THE PREPARATION OF 2,2 DIALKYL-ARYLIDENE-CYCLOALKANONES

[75] Inventors: Nikolaus Müller, Monheim; Thomas Essert, Overath, both of Germany

[73] Assignee: Bayer Aktiengesellschaft, Leverkusen, Germany

[21] Appl. No.: 667,894

[22] Filed: Jun. 20, 1996

[30] Foreign Application Priority Data

Jun. 28, 1995 [DE] Germany .................... 19523449.9

[51] Int. Cl.$^6$ .................................................. C07C 45/45
[52] U.S. Cl. .................... 568/316; 558/414; 568/315; 568/306
[58] Field of Search ................... 558/414; 568/308, 568/315, 316, 348, 391, 396, 393

[56] References Cited

U.S. PATENT DOCUMENTS

| | | | |
|---|---|---|---|
| 3,983,175 | 9/1976 | Tamai et al. | 568/393 |
| 4,305,034 | 12/1981 | Nakayama et al. | 568/316 |
| 4,686,291 | 8/1987 | Lantzsch et al. | 568/393 |

FOREIGN PATENT DOCUMENTS

| | | |
|---|---|---|
| 0378953 | 7/1990 | European Pat. Off. . |
| 0467791 | 1/1992 | European Pat. Off. . |
| 0467792 | 1/1992 | European Pat. Off. . |
| 0626363 | 11/1994 | European Pat. Off. . |

OTHER PUBLICATIONS

S. Boatman, et al., Organic Syntheses, vol. 48, pp. 40–46.
S. Boatman, et al., Alkylations at the α'–Methylene or Methinyl Group of α–Formyl Cyclic Ketones through Their Dicarbanions. Angular Alkylations[1], Journal of the American Chemical Society, 87:1, pp. 82–86, (1965).
J.–M. Conia, Alcoylation des cétones par l'intermédiare de l'amylate tertiaire de sodium (1st mémoire), Bull. Soc. France, pp. 533–537, (1950).
J.–M. Conia L'effet stérique dans l'alcoylation des cétones, Bull. Soc. Chem. France, pp. 1040–1047, (1956).
E.J. Corey, et al., Methylsulfinyl Carbanion ($CH_3$–SO–$CH_2$–). Formation and Applications to Organic Synthesis, J. Am. Chem. Soc., 87, pp. 1345–1353, (1965).
J. Am. Chem. Soc. vol. 84, pp. 866–867, (1962).

Primary Examiner—James H. Reamer
Attorney, Agent, or Firm—Sprung Horn Kramer & Woods

[57] ABSTRACT

A particularly advantageous process for the preparation of 2,2-dialkyl-arylidene-cycloalkanones is characterized in that 2-alkyl-arylidene-cycloalkanones are reacted with alkyl halides in the presence of metal hydroxides and tertiary alcohols.

14 Claims, No Drawings

PROCESS FOR THE PREPARATION OF 2,2 DIALKYL-ARYLIDENE-CYCLOALKANONES

The present invention relates to a particularly advantageous process for the preparation of 2,2-dialkyl-arylidene-cycloalkanones from the corresponding 2-alkyl-arylidene-cycloalkanones by alkylation.

It already known to prepare 2,2-dialkyl-arylidene-cycloalkanones by reacting 1-alkyl-arylidene-cycloalkanones with alkyl halides in the presence of very strong bases. Thus, EP-A1 378 953 describes the preparation of 2,2-diallyl-5-(4-chlorobenzylidene)-cyclopentanone by reacting 2-allyl-5-(4-chlorobenzylidene)-cyclopentanone with allyl chloride in the presence of sodium hydride in toluene/tert-amyl alcohol, and the preparation of 2,2-dimethyl-6-(4-chlorobenzylidene)-cyclohexanone from 2-methyl-6-(4-chlorobenzylidene)-cyclohexanone by alkylation with methyl iodide in the presence of toluene/tert-amyl alcohol and sodium hydride.

The introduction of an n-butyl radical using n-butyl bromide in 2-methyl-6-hydroxy-methylene-cyclohexanone is likewise successful only with the very strong base potassium amide in ammonia (see Org. Synth. 48, 40 (1968) and J. Am. Chem. Soc. 87, 82 (1965). The compounds described have the disadvantage that, as with all relatively weakly methylene-active compounds, it is necessary to employ very strong bases such as alkali metal amides, alkali metal hydrides, triphenylmethides of the alkali metals, or tertiary alkoxides. Operating with such bases on the industrial scale is difficult because of their high reactivity, and special measures must be taken, such as working under inert gas or the use of special solvents. Furthermore, because of their complex preparation these bases are expensive, so that using them is uneconomic.

The alkali metal hydrides which are used most frequently, especially sodium hydride, must be handled with particular care owing to the evolution of hydrogen.

The alkali metal tert-alkoxides mentioned in the literature, which can be employed in the corresponding alcohol as solvent, have the grave disadvantage that, for the purpose of alkylation, the keto compound must be converted completely into its enolate, and the basicity of the tertiary alkoxides is usually insufficient for this purpose. As a result, secondary reactions take place between the enolate ion and the free ketone, for example aldol condensations and Michael additions, which lead to considerable losses in yield and necessitate laborious cleaning operations (see Bull. Soc. Chim. Franc. 533–537 (1950) and 1040 (1956)).

Triphenylmethylides of the alkali metals have in particular the disadvantage of a high proportion of triphenylmethane which is unavoidably produced. The sodium salt of dimethyl sulphoxide, which is employed in some cases, has the disadvantage that, as a carbanion, it adds on to the carbonyl group itself and can also be alkylated itself. Furthermore, this compound has to be formed first from dimethyl sulphoxide and sodium hydride in a preceding reaction, in which case one is again presented with the problem of the use of alkali metal hydrides (see J. Am. Chem. Soc. 87, 1345 (1965) and 844, 866 (1962)).

2,2-Dialkyl-arylidene-cycloalkanones can additionally be prepared by aldol condensation of 2,2-dialkyl-substituted cycloalkanones with aromatic aldehydes. Thus, EP-A1 467 791 and EP-A1 467 792 describe the preparation of 2,2-dimethyl-5-(4-chlorobenzylidene)-cyclopentanone. The problems of this process, which is simple per se, lie in the difficulty of obtaining the starting materials. Owing to the presence of two methylene-active α positions, 2,2-dialkylcyclo-alkanones have to be reversibly blocked, which requires two additional reaction stages (see Org. Synth. 48, 40 (1968)). An alternative preparation of 2,2-dialkyl-cycloalkanones which is described is the cyclization of 2,2-dialkyl-α,ω-dicarboxylic esters or the thermal cyclization of the corresponding carboxylic acids with catalysis by metal salts (see EP-A1 626 363). In this case, however, the problem shifts to the obtainability of the 2,2-dialkyl-substituted dicarboxylic acids or their esters, which is even more difficult than that of the 2,2-dialkyl-substituted cycloalkanones.

A process has now been found for the preparation of 2,2-dialkyl-arylidene-cyclo-alkanones of the formula

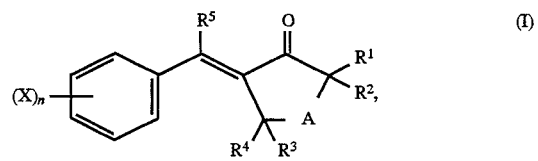

(I)

in which

A represents optionally substituted —(CH$_2$)—$_x$ where x=1, 2 or 3,

R$^1$ and R$^2$ represent identical or different, optionally substituted C$_1$–C$_4$-alkyl or C$_3$–C$_7$-cycloalkyl radicals, R$^3$, R$^4$ and R$^5$ are identical or different and represent hydrogen or optionally substituted C$_1$–C$_4$-alkyl or C$_3$–C$_7$-cycloalkyl, X represents halogen, cyano, nitro, C$_1$–C$_4$-alkyl, C$_1$–C$_4$-halogenoalkyl, C$_1$–C$_4$-alkoxy or C$_1$–C$_4$-halogenoalkoxy, and, when two or more radicals X are present, they may be identical or different, and n represents zero or an integer from 1 to 5, which is characterized in that 2-alkyl-arylidene-cycloalkanones of the formula

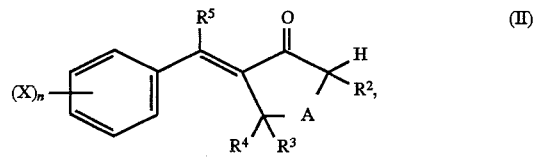

(II)

in which the symbols used have the meaning given for formula (I), are reacted with alkyl halides in the presence of metal hydroxides and tertiary alcohols.

A can optionally contain one or more identical or different substituents from the group consisting of C$_1$–C$_4$-alkyl and C$_3$–C$_7$-cycloalkyl, it being possible for C$_1$–C$_4$-alkyl in turn to be optionally substituted by halogen or C$_1$–C$_4$-alkoxy and for C$_3$–C$_7$-cycloalkyl in turn to be optionally substituted by halogen, C$_1$–C$_4$-alkyl or C$_1$–C$_4$-alkoxy. A preferably represents —CH$_2$—, —CH$_2$—CH$_2$— or —CH$_2$—CH$_2$—CH$_2$—; in other words, 2-alkyl-arylidene-cyclopentanones, -cyclohexanones or -cycloheptanones of the formula (II) are preferably reacted to 2,2-dialkyl-5-arylidene-cyclopentanones, 2,2-dialkyl-6-arylidene-cyclohexanones or 2,2-dialkyl-7-arylidene-cycloheptanones of the formula (I).

Where R$^1$ and R$^2$ represent C$_1$–C$_4$-alkyl, the latter can optionally be substituted by halogen, C$_1$–C$_4$-alkoxy, halogeno-C$_1$–C$_4$-alkoxy, C$_2$–C$_4$-alkenyl, C$_2$–C$_4$-alkinyl, halogeno-C$_2$–C$_4$-alkenyl or halogeno-C$_2$–C$_4$-alkinyl. Where R$^1$ and R$^2$ represent C$_3$–C$_7$-cycloalkyl, the latter can be substituted by halogen, C$_1$–C$_4$-alkoxy or C$_1$–C$_4$-alkyl. R$^1$ and R$^2$ independently of one another preferably represent unsubstituted C$_1$–C$_4$-alkyl or unsubstituted C$_2$–C$_4$-alkenyl.

Where $R^3$, $R^4$ and $R^5$ represent $C_1$–$C_4$-alkyl, the latter can optionally be substituted by halogen or $C_1$–$C_4$-alkoxy. Where $R^3$, $R^4$ and $R^5$ represent $C_3$–$C_7$-cycloalkyl, the latter can optionally be substituted by halogen, $C_1$–$C_4$-alkyl or $C_1$–$C_4$-alkoxy. $R^3$, $R^4$ and $R^5$ preferably represent hydrogen.

X preferably represents fluorine, chlorine, cyano or $C_1$–$C_4$-alkyl.

n preferably represents zero, 1 or 2. If n=1, X is preferably in position 4. If n=2, X is preferably in positions 2 and 4.

Except in the case of alkyl halides, halogen can in all definitions be, for example, fluorine, chlorine or bromine. It preferably represents fluorine or chlorine.

Particularly preferred starting compounds of the formula (II) are: 2-methyl- and 2-ethyl-5-(4-fluoro-, 4-chloro-, 4-cyano- and 3,4-dichloro-benzylidene)-cyclopentanone, -cyclohexanone and -cycloheptanone.

2-Alkyl-arylidene-cycloalkanones of the formula (II) are known compounds or can be prepared similarly to known compounds.

A preferred process for the preparation of 2-alkyl-arylidene-cycloalkanones of the formula (II) is illustrated, taking the preparation of 2-alkyl-arylidene-cyclopentanones by way of example, as follows: first of all a 2-alkylcyclopentanone is prepared by reacting adipic esters with an alcoholate to obtain the salt of a cyclopentanone-2-carboxylic ester, which is alkylated without isolation beforehand to give a 2-alkyl-cyclopentanone-2-carboxylic ester, which is decarboxylated without isolation beforehand by treatment with an acid and heating. The 2-alkyl-2-cyclopentanone thus obtained is then reacted with an aromatic carbonyl compound in the presence of a basic catalyst. This procedure is the subject of other patent applications.

Examples of alkyl halides which can be employed are those of the formula (III)

$$R^1\text{—}Y \qquad (III),$$

in which
$R^1$ has the broadest meaning given above and
Y represents chlorine, bromine or iodine.

Preference is given to alkyl halides of the formula (III) in which $R^1$ has the preferred meaning given above and Y represents chlorine or bromine. Particularly preferred alkyl halides of the formula (III) are: methyl chloride, methyl bromide, ethyl chloride, ethyl bromide, n-propyl chloride, iso-propyl chloride, n-propyl bromide, iso-propyl bromide, 1-chlorobutane, 2-chlorobutane, isobutyl chloride, 1-bromobutane, 2-bromobutane, isobutyl bromide, allyl chloride, allyl bromide, crotyl chloride, crotyl bromide, propargyl chloride and propargyl bromide.

It is preferable, in addition to alkyl halides of the formula (III) where Y=chlorine, to employ alkali metal iodides, preferably potassium iodide and/or sodium iodide. Based on the compound of the formula (II) employed it is possible, for example, to employ from 0.1 to 50 mol-%, preferably from 1 to 25 mol-% and, with particular preference, from 2.5 to 10 mol-%, of alkali metal iodides.

Alkyl halides are generally employed in at least a stoichiometric quantity, for example from 1 to 30 mol of alkyl halide per mole of compound of the formula (II) employed. This quantity is preferably from 1.2 to 10 mole, in particular from 1.3 to 2.5 mol.

Examples of metal hydroxides which can be employed are alkali metal and alkaline earth metal hydroxides, such as lithium hydroxide, sodium hydroxide, potassium hydroxide, caesium hydroxide, magnesium hydroxide, calcium hydroxide, strontium hydroxide and barium hydroxide. Sodium, potassium, magnesium and calcium hydroxide are preferred; potassium hydroxide is particularly preferred.

Metal hydroxides are generally employed in at least an equimolar quantity, preferably in excess. For each mole of compound of the formula (II) employed it is possible, for example, to employ from 1.09 to 10 equivalents of metal hydroxide. This quantity is preferably from 1.1 to 5 equivalents, in particular from 1.2 to 2.5 equivalents.

Examples of tertiary alcohols which can be employed are those of the formula (IV)

in which $R^6$, $R^7$ and $R^8$ are identical or different and each represent $C_1$–$C_4$-alkyl, $C_2$–$C_4$-alkenyl, $C_2$–$C_4$-alkinyl, $C_3$–$C_7$-cycloalkyl, $C_6$–$C_{10}$-aryl or $C_7$–$C_{12}$-aralkyl, all of which radicals can optionally be substituted by $C_1$–$C_4$-alkoxy and/or halogen. The radicals $R^6$ and $R^7$, $R^7$ and $R^8$ or $R^6$, $R^7$ and $R^8$ can also in each case form, together with the carbon atom lying between them, a ring containing 5 to 7 carbon atoms.

Preferred tertiary alcohols are: tert-butanol, tert-amyl alcohol, methyldiethyl-carbinol, triethylcarbinol, 2-methyl-2-pentanol, 2-methyl-2-hexanol, 1-methyl-1-cyclopentanol and 1-methyl-1-cyclohexanol. Tert-butanol and tert-amyl alcohol are particularly preferred.

The tertiary alcohols can be employed as such or as a mixture with inert solvents. Examples of inert solvents are: aliphatic hydrocarbons such as cyclohexane, $C_6$–$C_{12}$-alkanes and mixtures thereof; aromatic hydrocarbons such as benzene, toluene, xylenes, cumene, diisopropylbenzenes and ethylbenzene; halogenated aromatic compounds such as chlorobenzene, dichlorobenzenes, trichlorobenzenes and chlorotoluenes; dialkyl, aralkyl and diaryl ethers, such as diisopropyl ether, methyl tert-butyl ether, anisole, phenetol and diphenyl ether; cyclic ethers such as tetrahydrofuran, tetrahydropyran and 1,4-dioxane, and sulphones such as dimethyl sulphoxide and tetramethylene sulphone.

Based on tertiary alcohol, it is possible for example to add from 0.01 to 50% by weight, and preferably from 0.1 to 20% by weight, of inert solvent. Particular preference is given to employing tertiary alcohols without additions of inert solvent.

The tertiary alcohols can be used, for example, in quantities of from 100 to 5000 g per 100 g of compound of the formula (II) employed. The quantity of tertiary alcohol is preferably chosen so as to give a readily stirrable reaction mixture.

The process according to the invention can be carried out, for example, at temperatures in the range from −20° to +200° C. Preferred temperatures are from 0° to 100° C., in particular from 20° to 50° C.

The process according to the invention can be carried out, for example, at pressures of from 1 to 100 bar. If it is desired to carry out the process according to the invention at temperatures at which certain constituents of the reaction mixture are gaseous at atmospheric pressure, then it is necessary to work in closed vessels under at least the autogenous pressure. It is frequently advantageous to inject inert gases such as nitrogen, helium or argon and to work at from 5 to 50 bar, in, particular at from 10 to 30 bar.

The duration of reaction depends in each individual case on the composition of the reaction mixture and on the reaction conditions. For example, it can be between 1 and 48 hours. It is often in the range from 3 to 30 hours and, when working at from 10° to 50° C., is often in the range from 5 to 24 hours.

The reaction mixture which is present after the end of the reaction according to the invention can, for example, be worked up such that first of all tertiary alcohol and any inert solvent present are separated off. Optionally under reduced pressure, water is added to the residue, and the crystalline product which forms is filtered off with suction, washed and dried. If it is desired to purify the product still further, it can be recrystallized.

A preferred embodiment of the process according to the invention is illustrated below, by way of example, with reference to the reaction of 2-methyl-5-(4-chlorobenzylidene)cyclopentanone with methyl chloride/potassium iodide:

2-methyl-5-(4-chlorobenzylidene)-cyclopentanone, tert-butanol and potassium iodide are placed in a pressure autoclave, potassium hydroxide is added and methyl chloride is injected with stirring. Stirring is continued for a certain time at room temperature or slightly elevated temperature. The majority of the tert-butanol is then distilled off and water is added to the suspension which remains. The crystalline product is filtered off with suction, washed and dried. For further purification it is recrystallized, for example, from an alcohol.

It is extremely surprising that the alkylation of not particularly methylene-active ketones according to the invention can be carried out using alkali metal hydroxides as bases, especially since alkali metal alcoholates, which are more basic by a multiple factor (see J. March, Advanced Organic Chemistry, 4th Edition, New York 1992 and the literature cited therein), are inadequate for this purpose. The use of alkali metal tert-alkoxides, for example potassium tert-butylate in tert-butanol, which is cited fairly frequently, can not be compared with the use of potassium hydroxide in tert-butanol, since the equilibrium

KOH+(CH₃)₃COH⇌KOC(CH₃)₃+H₂O lies almost completely on the left-hand side. Even in the system comprising potassium tert-butylate/tert-butanol, it is not possible to convert the ketone completely into the enolate. If the enolate ion and unchanged ketone are present alongside one another, secondary reactions can be expected to an increased extent (see Bull. Soc. Chim. Fr. 533, 537 (1950) and 1040 (1956)).

The use of the much weaker alkali metal hydroxides, therefore, should promote secondary reactions to a greater extent. It is all the more surprising that the alkylation according to the invention, using alkali metal hydroxides as base, nevertheless takes place under very mild conditions and with high yields. The process according to the invention is a method which is extremely simple to carry out for the preparation of 2,2-dialkyl-arylidene-cycloalkanones of the formula (I) in high yields and under mild conditions.

The use of difficult-to-handle bases such as metal hydrides or metal amides, which is possible only with increased expenditure on safety, is avoided. Relatively large quantities of very special solvents, such as DMSO, DM2F or ammonia, which would become contaminated with water on working up the reaction mixture and would then have to be recovered, a laborious operation, are unnecessary.

The possibility of the use of alkyl chlorides in the presence of alkali metal iodides leads to a cost saving and avoids operation with alkyl iodides, which requires special consideration because of their carcinogenicity.

2,2-Dialkyl-arylidene-cycloalkanones of the formula (I) are valuable intermediates for the production of pesticides, especially fungicides (EP-1 378 953, EP-A 1 467 791 and EP-A1 467 792). They can also be converted by reduction into 2,2-dialkyl-benzyl-cycloalkanones, which in turn can again be used as starting materials for fungicides (see EP-A1 267 778 and EP-A1 413 448).

EXAMPLE

Percentages are by weight unless stated otherwise.

Example 1

2,2-Dimethyl-5-(4-chlorobenzylidene)-cyclopentanone 106 g of 2-methyl-5-(4-chlorobenzylidene)-cyclopentanone, 49.5 g of 85% strength aqueous potassium hydroxide solution, 8.3 g of potassium iodide and 400 g of tert-butanol were weighed in succession into a 700 ml stainless steel autoclave, and 50.5 g of methyl chloride were injected at 20° C. The mixture was stirred at room temperature for 23 hours and then 300 ml of tert-butanol were distilled off at 20 mbar up to an overhead temperature of max. 50° C. 400 ml of water were added to the residue, and the mixture was stirred thoroughly. The resulting suspension was filtered off over a suction filter, and the filter cake was washed twice with 200 ml of water each time and dried. 112.8 g of a pale beige solid were thus obtained with a purity of 89.5%. The yield of the crude product was 90.2% of theory.

For purification the crude product was suspended in 250 ml of methanol and the suspension was heated at reflux temperature for 30 min and then cooled. The product which had separated out was filtered off, washed with methanol and dried. 86 g of pure product were thus obtained, with a melting point of 120° to 122° C.

Example 2

2,2-Dimethyl-6-benzylidene-cyclohexanone 66 g of 85% strength potassium hydroxide solution and 750 ml of tert-butanol were placed in a 1 l 4-necked flask, and the mixture was heated briefly at reflux with stirring. Then 8.3 g of potassium iodide were added, the mixture was cooled to room temperature and 200 g of 2-methyl-6-benzylidene-cyclohexanone were added. 101 g of methyl chloride were passed in at room temperature over 8 hours. The mixture was subsequently stirred at room temperature for 8 hours, and then 450 ml of tert-butanol were distilled off. 500 ml of water were added to the residue, the mixture was stirred thoroughly, and the product which separates out was filtered off with suction. Recrystallization from methanol gave 161 g (75% of theory) of pure product with a melting point of 79°–81° C., Examples 3 to 9

The procedure of Example 1 was followed to prepare the following products.

Example 3

2,2-Dimethyl-5-(4-fluorobenzylidene)-cyclopentanone, melting point 69° C.

Example 4

2,2-Diallyl-5-(4-chlorobenzylidene)-cyclopentanone, oil.

Example 5

2,2-Dimethyl-5-(3,4-dichlorobenzylidene)-cyclopentanone, oil.

Example 6

2-Ethyl-2-methyl-5-(4-chlorobenzylidene)-cyclopentanone, melting point 83°–84° C.

Example 7

2,2-Dimethyl-5-(4-cyanobenzylidene)-cyclopentanone, oil.

Example 8

2-Ethyl-2-methyl-6-(4-chlorobenzylidene)-cyclohexanone, melting point 71°–72° C.

Example 9

2,2-Dimethyl-7-(4-chlorobenzylidene)-cycloheptanone, melting point 63° C.

What is claimed is:

1. A process for the preparation of a 2,2-dialkyl-arylidene-cyclo-alkanone of the formula

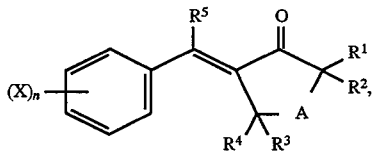 (I)

in which

A represents —(CH$_2$)—$_x$ where x=1, 2 or 3, and which is unsubstituted or substituted with one or more identical or different substituents from the group consisting of C$_1$–C$_4$-alkyl and C$_3$–C$_7$-cycloalkyl, it being possible for C$_1$–C$_4$-alkyl in turn to be unsubstituted or substituted by halogen or C$_1$–C$_4$-alkoxy and for C$_3$–C$_7$-cycloalkyl in turn to be unsubstituted or substituted by halogen, C$_1$–C$_4$-alkyl or C$_1$–C$_4$-alkoxy, R$^1$ and R$^2$ represent identical or different, C$_1$–C$_4$-alkyl or C$_3$–C$_7$-cycloalkyl radicals, which are unsubstituted or C$_1$–C$_4$-alkyl is substituted by halogen, C$_4$–C$_4$-alkoxy, halogeno-C$_1$–C$_4$-alkoxy, C$_2$–C$_4$-alkenyl, C$_2$–C$_4$-alkinyl, halogeno-C$_2$–C$_4$-alkenyl or halogeno-C$_2$–C$_4$-alkinyl, or C$_3$–C$_7$-cycloalkyl is substituted by halogen, C$_1$–C$_4$-alkoxy or C$_1$–C$_4$-alkyl, R$^3$, R$^4$ and R$^5$ are identical or different and represent hydrogen, C$_1$–C$_4$-alkyl or C$_3$–C$_7$-cycloalkyl, where C$_1$–C$_4$-alkyl and C$_3$–C$_7$-cycloalkyl can be unsubstituted or C$_1$–C$_4$-alkyl is substituted by halogen or C$_1$–C$_4$-alkoxy or C$_3$–C$_7$-cycloalkyl is substituted by halogen, C$_1$–C$_4$-alkyl or C$_1$–C$_4$-alkoxy, X represents halogen, cyano, nitro, C$_1$–C$_4$-alkyl, C$_1$–C$_4$-halogenoalkyl, C$_1$–C$_4$-alkoxy or C$_1$–C$_4$-halogeno-alkoxy, and, when two or more radicals X are present, they may be identical or different, and n represents zero or an integer from 1 to 5, in which a 2-alkyl-arylidene-cycloalkanone of the formula

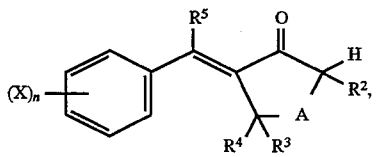 (II)

in which the symbols used have the meaning given for formula (I), is reacted with an alkyl halide in the presence of a metal hydroxide and a tertiary alcohol.

2. The process of claim 1, in which

X represents fluorine, chlorine, cyano or C$_1$–C$_4$-alkyl and n represents zero, 1 or 2.

3. The process of claim 1, in which the compound of the formula (II) employed is 2-methyl- or 2-ethyl-5-(4-fluoro-, 4-chloro-, 4-cyano- and 3,4-dichloro-benzylidene)-cyclopentanone, -cyclohexanone or -cycloheptanone.

4. The process of claim 1, in which the alkyl halide employed is of the formula (III)

R$^1$—Y (III), in which

R$^1$ has the meaning given in claim 1 and

Y represents chlorine, bromine or iodine.

5. The process of claim 4, in which in addition to an alkyl halide of the formula (III) where Y=chlorine, from 0.1 to 50 mol-% of an alkali metal iodide is employed (based on the compound of the formula (II)).

6. The process of claim 1, in which the alkyl halide is employed in a quantity of from 1 to 30 mol based on 1 mol of the compound of the formula (II) employed.

7. The process of claim 1, in which the metal hydroxide is an alkali metal or alkaline earth metal hydroxide which is employed in at least an equimolar quantity.

8. The process of claim 1, in which the tertiary alcohol employed is of the formula (IV)

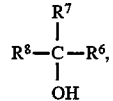 (IV)

in which

R$^6$, R$^7$ and R$^8$ are identical or different and each represent C$_1$–C$_4$-alkyl, C$_2$–C$_4$-alkenyl, C$_2$–C$_4$-alkinyl, C$_3$–C$_7$-cycloalkyl, C$_6$–C$_{10}$-aryl or C$_7$–C$_{12}$-aralkyl, all of which radicals are unsubstituted or substituted by one or more of C$_1$–C$_4$-alkoxy and halogen, and the radicals R$^6$ and R$^7$ or R$^7$ and R$^8$ or R$^6$, R$^7$ and R$^8$ can in each case form, together with the carbon atom lying between them, a ring containing 5 to 7 carbon atoms.

9. The process of claim 1, in which the tertiary alcohol is employed as such.

10. The process of claim 1, in which the tertiary alcohol is employed as a mixture with an inert solvent.

11. The process of claim 1, in which the tertiary alcohol is employed in a quantity of from 100 to 5000 g per 100 g of compound of the formula (II).

12. The process of claim 1, which is carried out at a temperature in the range from −20° to +200° C.

13. The process of claim 1, which is carried out at a pressure in the range from 1 to 100 bar.

14. The process of claim 1, in which the reaction mixture which is present after the end of the reaction is worked up such that first of all tertiary alcohol and any inert solvent present are separated off, water is added to the residue, and the crystalline product which forms is filtered off with suction, washed and dried.

* * * * *

(12) EX PARTE REEXAMINATION CERTIFICATE (4901st)
United States Patent
Müller et al.

(10) Number: US 5,663,447 C1
(45) Certificate Issued: Feb. 3, 2004

(54) PROCESS FOR THE PREPARATION OF 2,2 DIALKYL-ARYLIDENE-CYCLOALKANONES

(75) Inventors: Nikolaus Müller, Monheim (DE); Thomas Essert, Overath (DE)

(73) Assignee: Bayer Aktiengesellschaft, Leverkusen (DE)

Reexamination Request:
No. 90/006,027, May 31, 2001

Reexamination Certificate for:
Patent No.: 5,663,447
Issued: Sep. 2, 1997
Appl. No.: 08/667,894
Filed: Jun. 20, 1996

(30) Foreign Application Priority Data

Jun. 28, 1995 (DE) .......................... 19523449.9

(51) Int. Cl.$^7$ ............................... C07C 45/45
(52) U.S. Cl. ................ 568/316; 558/414; 568/306; 568/315
(58) Field of Search ............................. 568/316, 315, 568/306; 558/414

(56) References Cited

U.S. PATENT DOCUMENTS

| | | | |
|---|---|---|---|
| 5,519,160 A | 5/1996 | Obara et al. | 560/51 |
| 5,663,447 A | 9/1997 | Muller et al. | 568/316 |

*Primary Examiner*—Shailendra Kumar

(57) ABSTRACT

A particularly advantageous process for the preparation of 2,2-dialkyl-arylidene-cycloalkanones is characterized in that 2-alkyl-arylidene-cycloalkanones are reacted with alkyl halides in the presence of metal hydroxides and tertiary alcohols.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–14 is confirmed.

* * * * *